(12) United States Patent
Foss et al.

(10) Patent No.: US 8,302,460 B2
(45) Date of Patent: Nov. 6, 2012

(54) MASS LOADING MONITOR

(75) Inventors: John F. Foss, East Lansing, MI (US);
Alan R. Lawrenz, East Lansing, MI (US)

(73) Assignee: Board of Trustees of Michigan State University, East Lansing, MI (US)

( * ) Notice: Subject to any disclaimer, the term of this patent is extended or adjusted under 35 U.S.C. 154(b) by 428 days.

(21) Appl. No.: 12/610,827

(22) Filed: Nov. 2, 2009

(65) Prior Publication Data

US 2010/0107738 A1 May 6, 2010

Related U.S. Application Data

(60) Provisional application No. 61/110,726, filed on Nov. 3, 2008.

(51) Int. Cl.
*G01N 37/00* (2006.01)
(52) U.S. Cl. ...................................................... 73/28.01
(58) Field of Classification Search .................. 73/28.01
See application file for complete search history.

(56) References Cited

U.S. PATENT DOCUMENTS

| | | | | |
|---|---|---|---|---|
| 5,713,325 A * | 2/1998 | Yoshida et al. | ............... | 123/295 |
| 5,720,254 A * | 2/1998 | Yoshida et al. | ............... | 123/305 |
| 5,775,289 A * | 7/1998 | Yoshida et al. | ............... | 123/305 |
| 6,865,926 B2 * | 3/2005 | O'Brien et al. | ............... | 73/23.27 |
| 6,944,524 B2 * | 9/2005 | Shier et al. | ............... | 700/301 |
| 6,980,902 B2 * | 12/2005 | Nakazawa | ............... | 701/102 |
| 7,021,298 B2 * | 4/2006 | Nakazawa et al. | ............... | 123/568.14 |
| 7,139,655 B2 * | 11/2006 | Nakazawa et al. | ............... | 701/102 |
| 7,257,987 B2 * | 8/2007 | O'Brien et al. | ............... | 73/23.41 |
| 7,275,415 B2 * | 10/2007 | Rhodes et al. | ............... | 73/28.01 |
| 7,549,317 B2 * | 6/2009 | Rhodes et al. | ............... | 73/23.31 |
| 7,621,171 B2 * | 11/2009 | O'Brien | ............... | 73/23.41 |
| 7,810,314 B2 * | 10/2010 | Brahma et al. | ............... | 60/276 |
| 2008/0053195 A1 * | 3/2008 | Matter et al. | ............... | 73/28.01 |

* cited by examiner

*Primary Examiner* — Hezron E Williams
*Assistant Examiner* — Rodney T Frank
(74) *Attorney, Agent, or Firm* — David D. Murray; Vivacqua Law, PLLC

(57) ABSTRACT

The present invention provides a mass loading monitor for measuring in real time the particulate, i.e., powder, dust and the like, content of air inside an industrial or commercial processing facility and providing a warning signal indicating the existence of a potentially explosive atmosphere in the facility. In a first embodiment, the mass loading monitor comprises two parallel cylinders, one of which is charged with clean, ambient air and the other of which is charged with air from within the facility containing dust, powder or other particulate matter. A piston resides within each cylinder and the pistons are commonly accelerated for a short distance during which time the pressure at each piston face is measured. The time integrals of the pressures from each of the piston faces are evaluated over the period: from rest to the time of discharge from the open end of the cylinders. The ratio of these integrals defines the difference in the densities within the cylinders. In a second embodiment, a single piston and cylinder assembly is first calibrated with clean air and subsequently filled with particulate laden air and the time integrals of the pressures on the piston face are similarly evaluated.

20 Claims, 13 Drawing Sheets

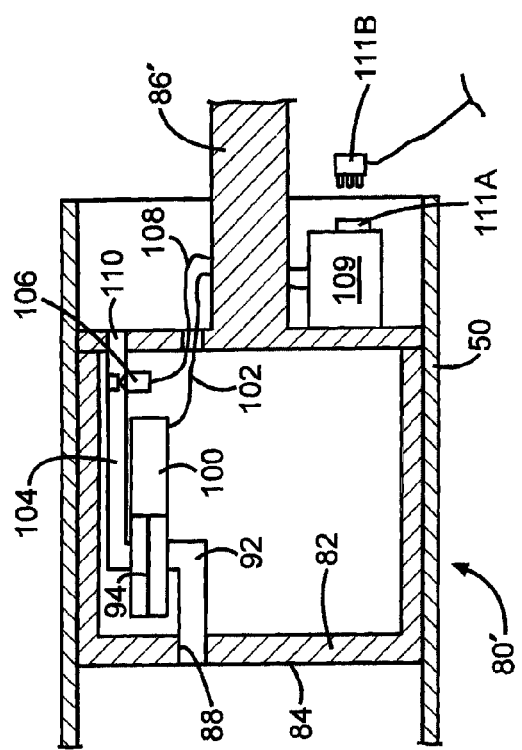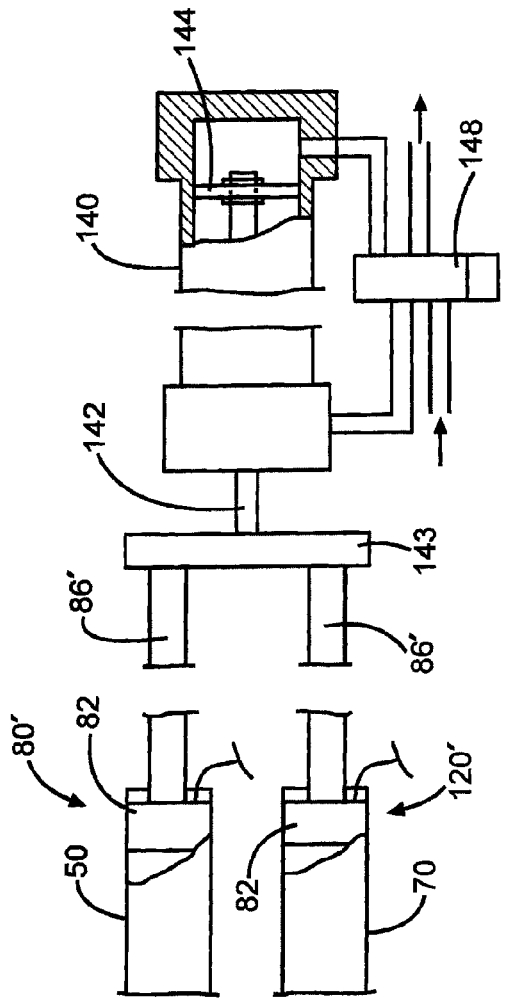

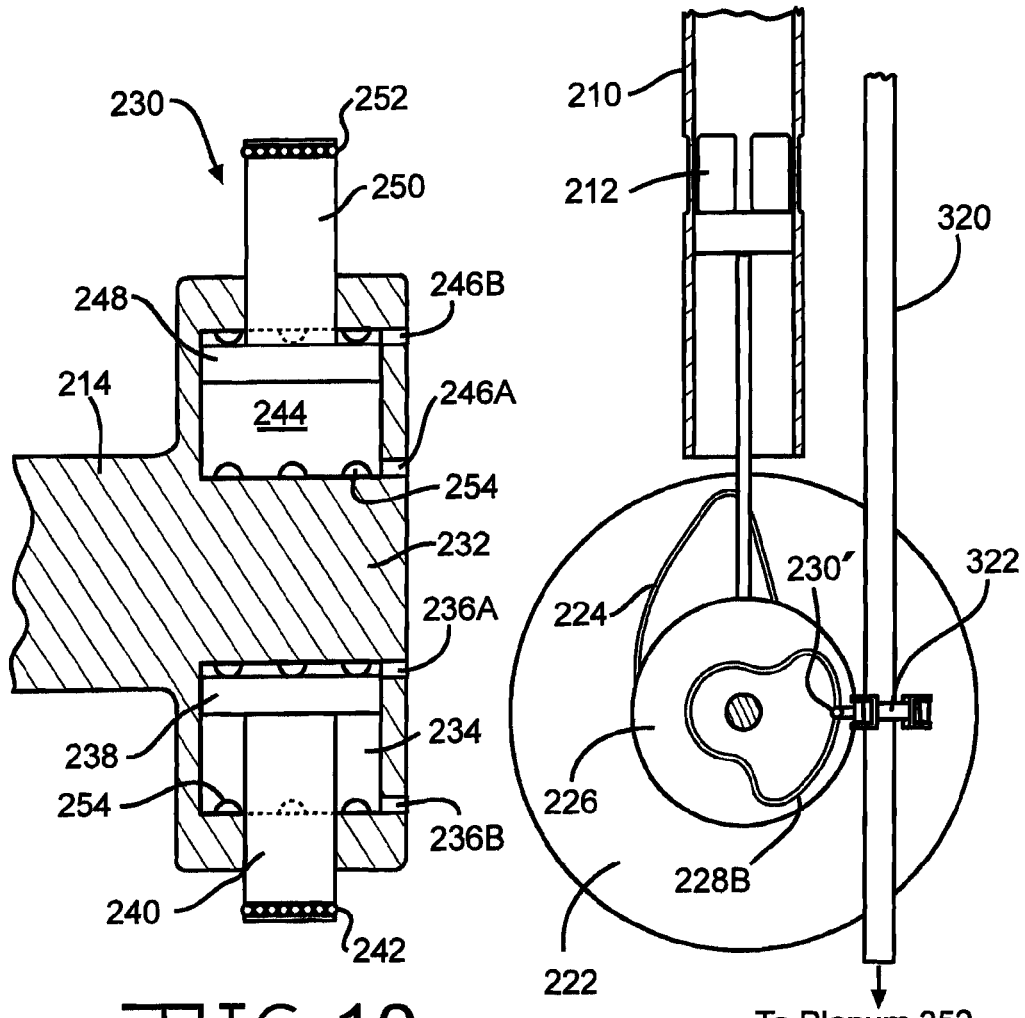
FIG. 10
FIG. 11
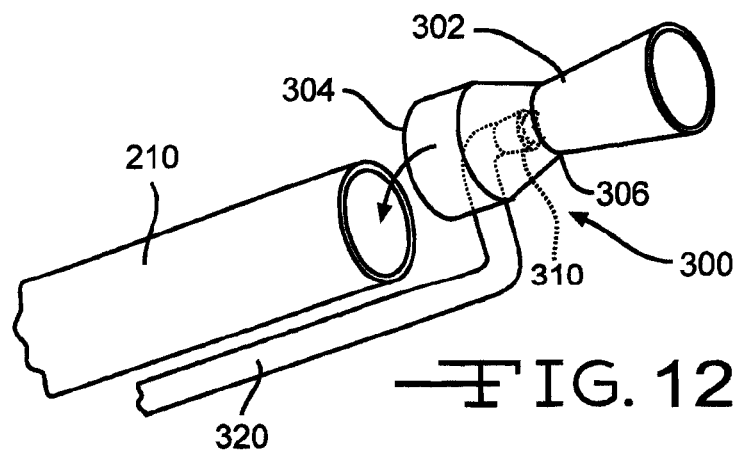
FIG. 12

MASS LOADING MONITOR

CROSS-REFERENCE TO RELATED APPLICATION

This patent application claims the benefit of U.S. Provisional Application No. 61/110,726, filed on Nov. 3, 2008. The disclosure of this provisional application is incorporated herein by reference.

FIELD

The present disclosure relates to devices for detecting concentrations of particulate matter in air and more particularly to a mass loading monitor for real time detection and warning of potentially explosive concentrations of dust, powder or particulate matter in air from industrial and commercial processes.

BACKGROUND

The statements in this section merely provide background information related to the present disclosure and may or may not constitute prior art.

Airborne dust or powder of, for example, sugar, grain and wood, escaping from industrial process machinery in a sufficient concentration can support rapid combustion and explosions. Such explosions typically occur in a confined or semi-confined space although an unbounded cloud can also support an explosion. Agricultural processes which occur at grain handling facilities such as transfer and storage depots, grain mills and cereal plants are particularly prone to this phenomenon. The following table highlights the losses over a recent ten year period (1996 to 2005) attributed to dust explosions in agricultural processing facilities in the United States.

TABLE 1

US AGRICULTURAL DUST EXPLOSION STATISTICS

|  | 1996 | 1997 | 1998 | 1999 | 2000 | 2001 |
|---|---|---|---|---|---|---|
| Number | 13 | 16 | 18 | 7 | 8 | 9 |
| Dead | 1 | 1 | 7 | 0 | 1 | 1 |
| Injured | 19 | 14 | 24 | 19 | 12 | 7 |
| Est. Damage to Facility ($ Mil) | 29.6 | 11.4 | 29.8 | 4.4 | 8.2 | 5.3 |

|  | 2002 | 2003 | 2004 | 2005 | 10-Year Total |
|---|---|---|---|---|---|
| Number | 8 | 8 | 6 | 13 | 106 |
| Dead | 1 | 2 | 0 | 2 | 16 |
| Injured | 8 | 8 | 4 | 11 | 126 |
| Est. Damage to Facility ($ Mil) | 5.1 | 10.1 | 2.7 | 56.2 | 162.8 |

Data Source: http://www.oznet.ksu.edu/dp_grsi/

Spray dryers are particularly vulnerable to this problem since they purposefully concentrate the powdered material before transferring it. The current response to this problem is to accept the possibility of an explosive event and incorporate, for example, explosion panels. These may either be passive devices—simply a weak component of the confining surface that gives way upon an explosion—or active devices that sense pressure in the device and release a panel. Alternatively, a dust suppressant may be routinely deployed in the spray dryer chamber.

Consideration of the foregoing current solutions to this problem leads one to the conclusion that an apparatus and technique to avoid this problem rather than to mitigate its effects would be a welcome addition to these industrial and commercial enterprises. The following disclosed and claimed invention is so directed.

SUMMARY

The present invention provides a mass loading monitor for measuring in real time the particulate, i.e., powder, dust and the like, content of air inside an industrial or commercial processing facility and providing a warning signal indicating the existence of a potentially explosive atmosphere in the facility. Optionally, the mass loading monitor may be configured to indicate the sensed level of particulate matter and to shut down the facility until the level of particulates drops to a safe level.

In an first embodiment, the mass loading monitor comprises two parallel cylinders, one of which is charged with clean, ambient air and the other of which is charged with air from within the facility containing dust, powder or other particulate matter. A piston resides within each cylinder and the pistons are commonly accelerated for a short distance during which time the pressure at each piston face is measured. The time integrals of the pressures from each of the piston faces are evaluated over the period: from rest to the time of discharge from the open end of the cylinders. The ratio of these integrals defines the difference in the densities within the cylinders. Lookup tables keyed to the type of material and relative humidity within the facility are then utilized to determine the explosion potential and provide an alarm or other indication that a predetermined concentration has been exceeded.

In a second embodiment, the same theory of operation is applied but only a single piston and cylinder assembly is utilized. Here, the single piston and cylinder assembly is first calibrated by determining the time integral of pressure with clean air at known temperature and barometric pressure. The assembly is then filled with particulate laden air and the time integral of pressure is compared to the calibration data and the density of the particulate laden air and its explosion potential is determined.

Thus it is an object of the present invention to provide an apparatus for monitoring the concentration of particulate matter in air.

It is a still further object of the present invention to provide an apparatus for monitoring the concentration of particulate matter in air in a processing facility for sugar, grain, wood and similar dust or powder producing materials.

It is a still further object of the present invention to provide an apparatus for monitoring the concentration of particulate matter in air in a processing facility for sugar, grain, wood and similar dust or powder producing materials and providing an alarm or other indication that a threshold concentration level has been reached or exceeded.

It is a still further object of the present invention to provide an apparatus for monitoring the concentration of particulate matter in air by accelerating samples of clean and particulate laden air to determine their time integrals of pressure and comparing the computed densities of the clean and particulate laden air.

It is a still further object of the present invention to provide an apparatus for monitoring the concentration of particulate matter in air having a pair of parallel cylinders in which a respective pair of pistons accelerate samples of clean and particulate laden air.

It is a still further object of the present invention to provide an apparatus for monitoring the concentration of particulate matter in air having a single piston and cylinder assembly that is calibrated with clean air and charged with particulate laden air.

It is a still further object of the present invention to provide a method for monitoring the concentration of particulate matter in air.

It is a still further object of the present invention to provide a method for monitoring the concentration of particulate matter in air by accelerating samples of clean and particulate laden air, determining the time integrals of pressure and comparing the computed air densities.

It is a still further object of the present invention to provide a method for monitoring the concentration of particulate matter in air in a processing facility for sugar, grain, wood and similar dust or powder producing materials and providing an alarm or other indication that a threshold concentration level has been reached or exceeded.

Further objects, advantages and areas of applicability will become apparent from the description provided herein. It should be understood that the description and specific examples are intended for purposes of illustration only and are not intended to limit the scope of the present disclosure.

DRAWINGS

The drawings described herein are for illustration purposes only and are not intended to limit the scope of the present disclosure in any way.

FIG. 3A is a fragmentary view of an alternate embodiment of a mass loading monitor according to the present invention;

Figure 4:
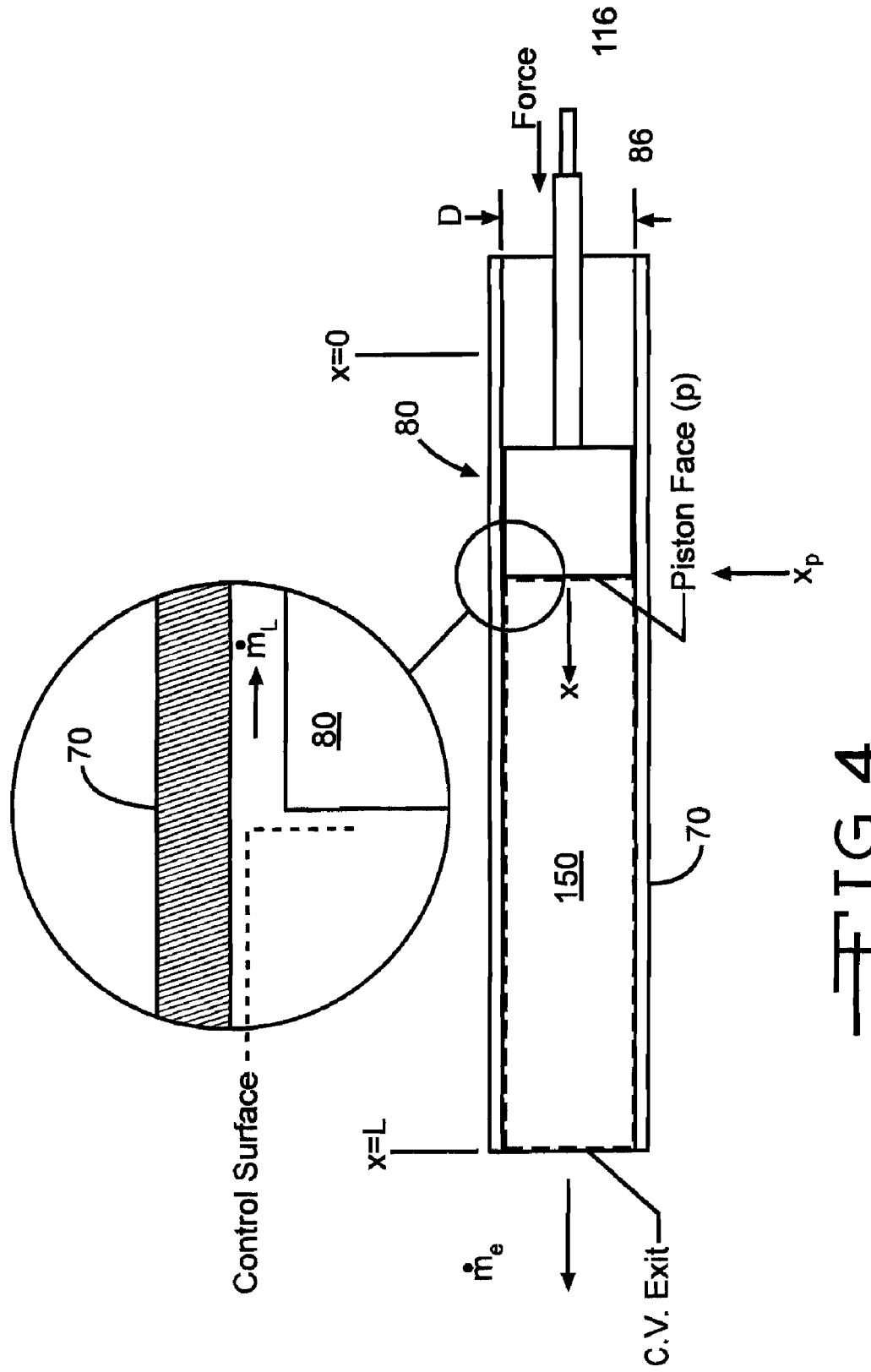
Figure 5:
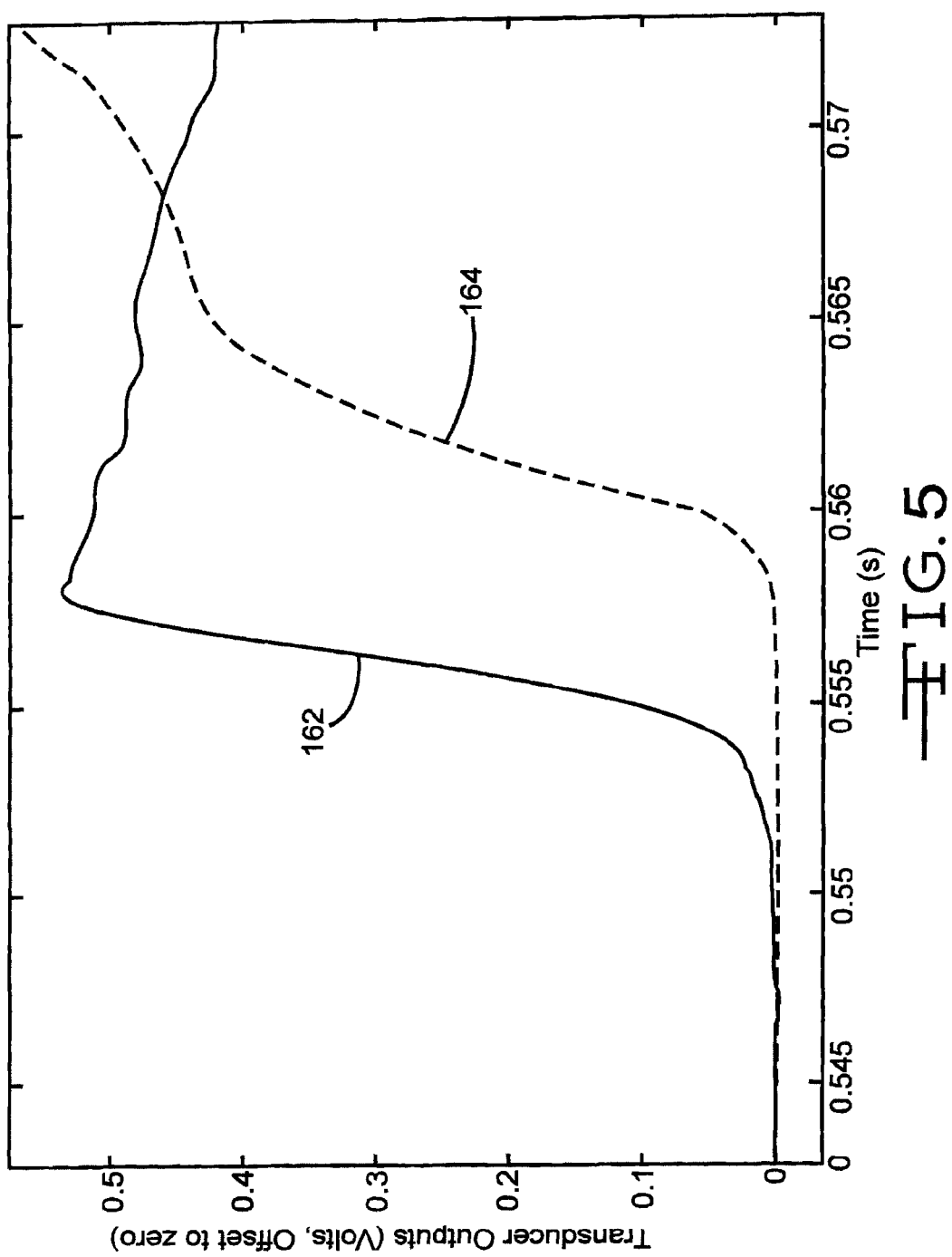
Figure 6:
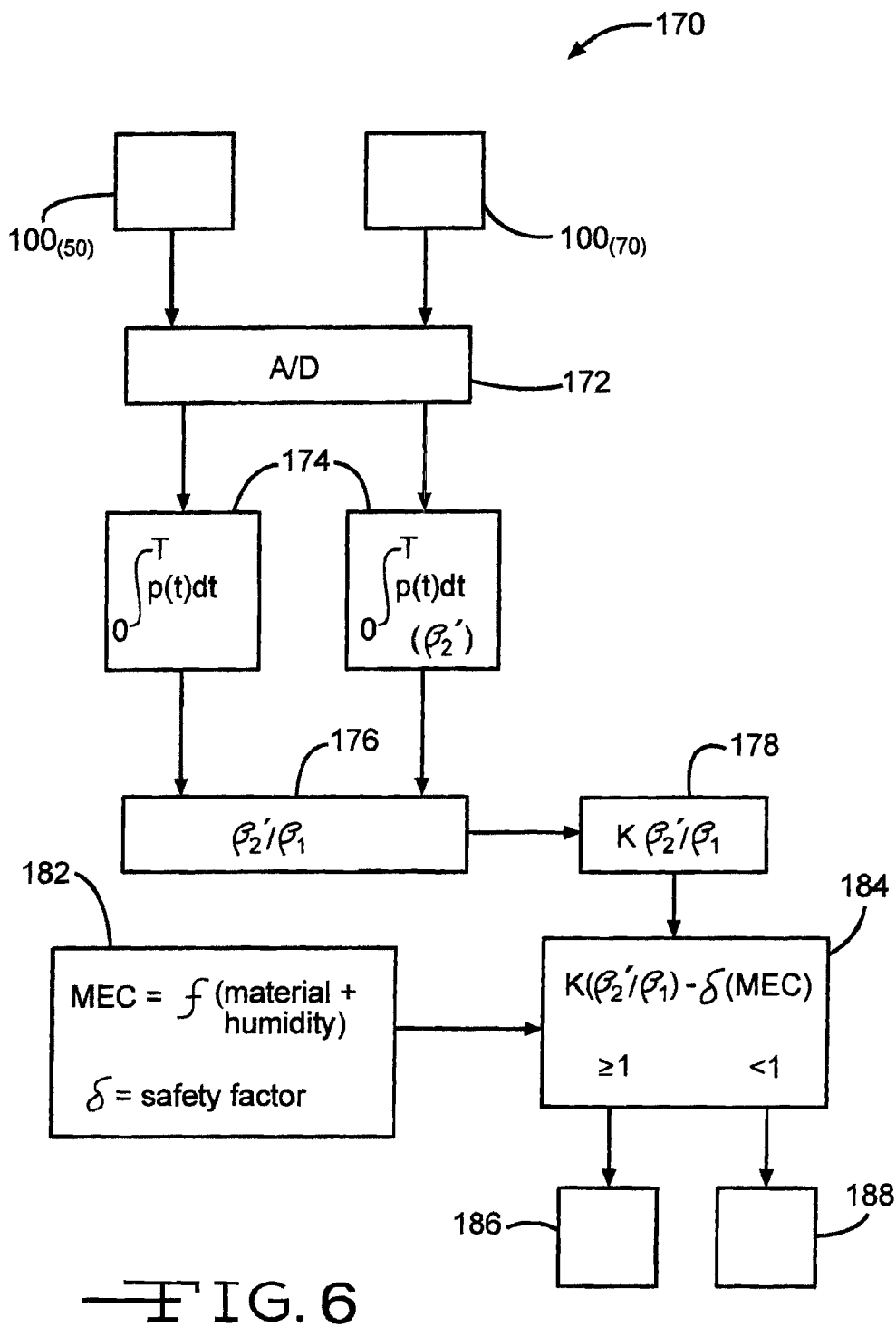
Figure 7:
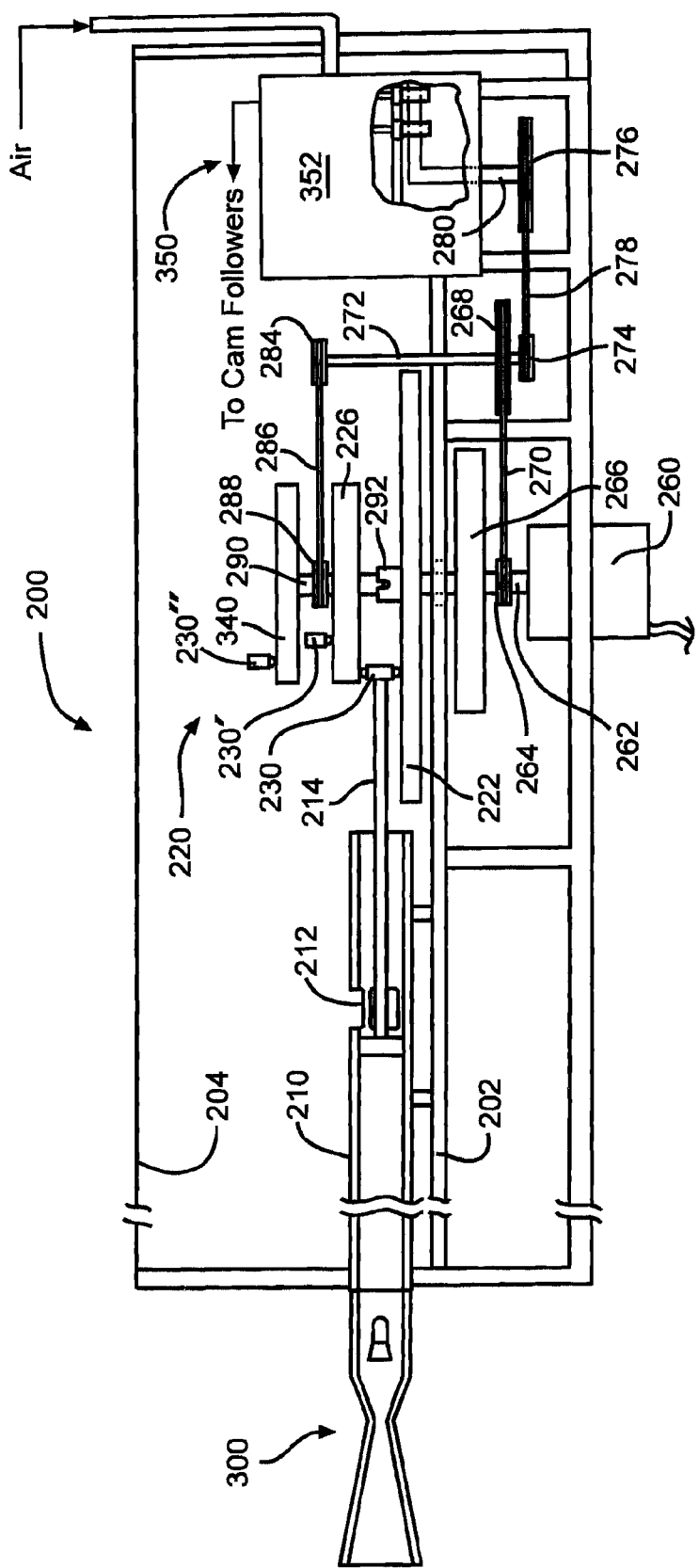
Figure 8:
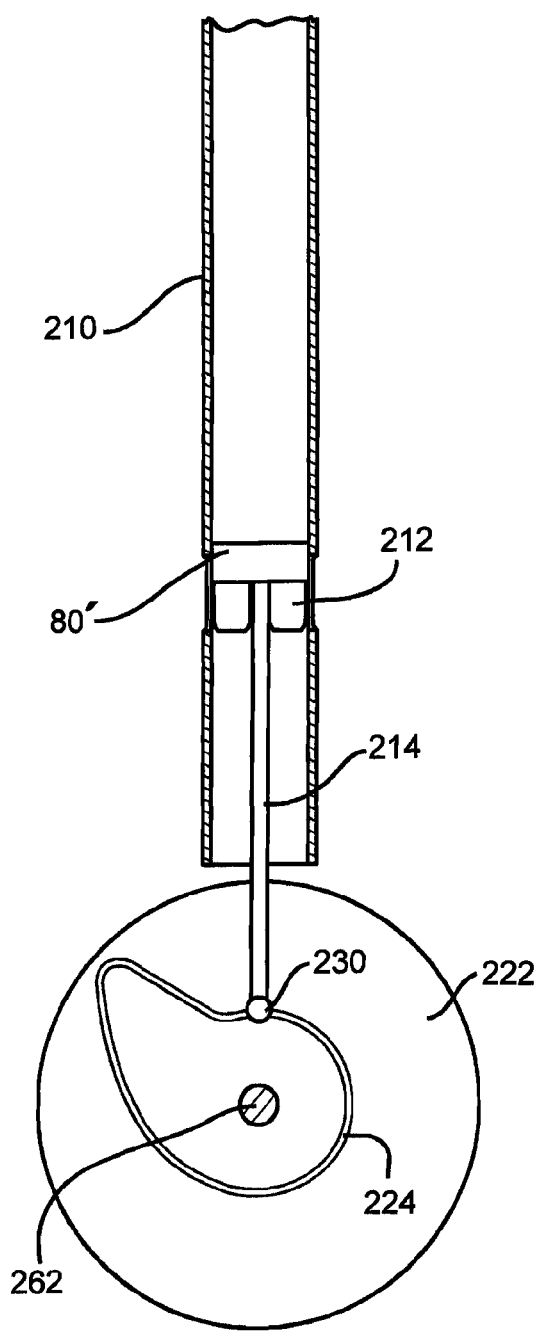
Figure 9:
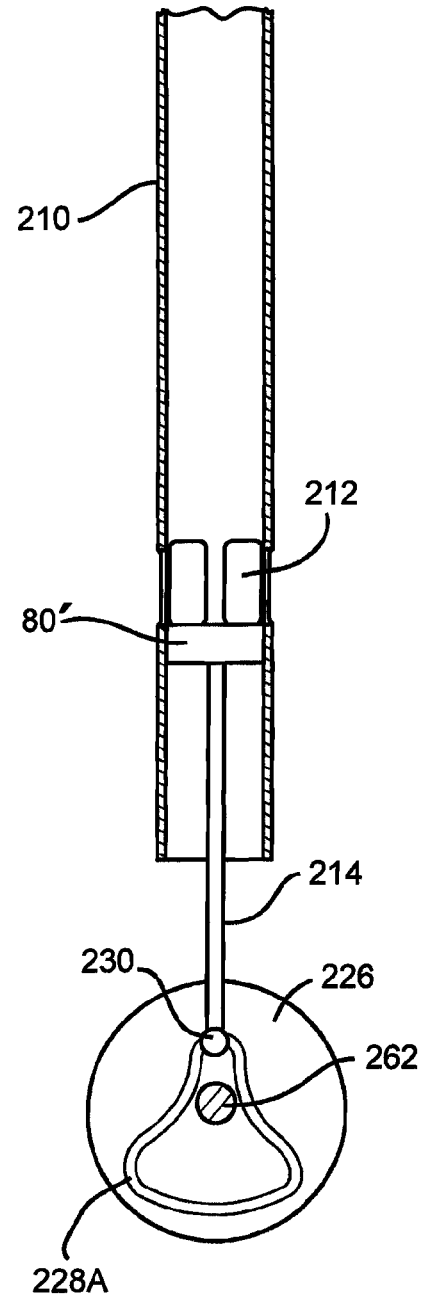
Figure 13:
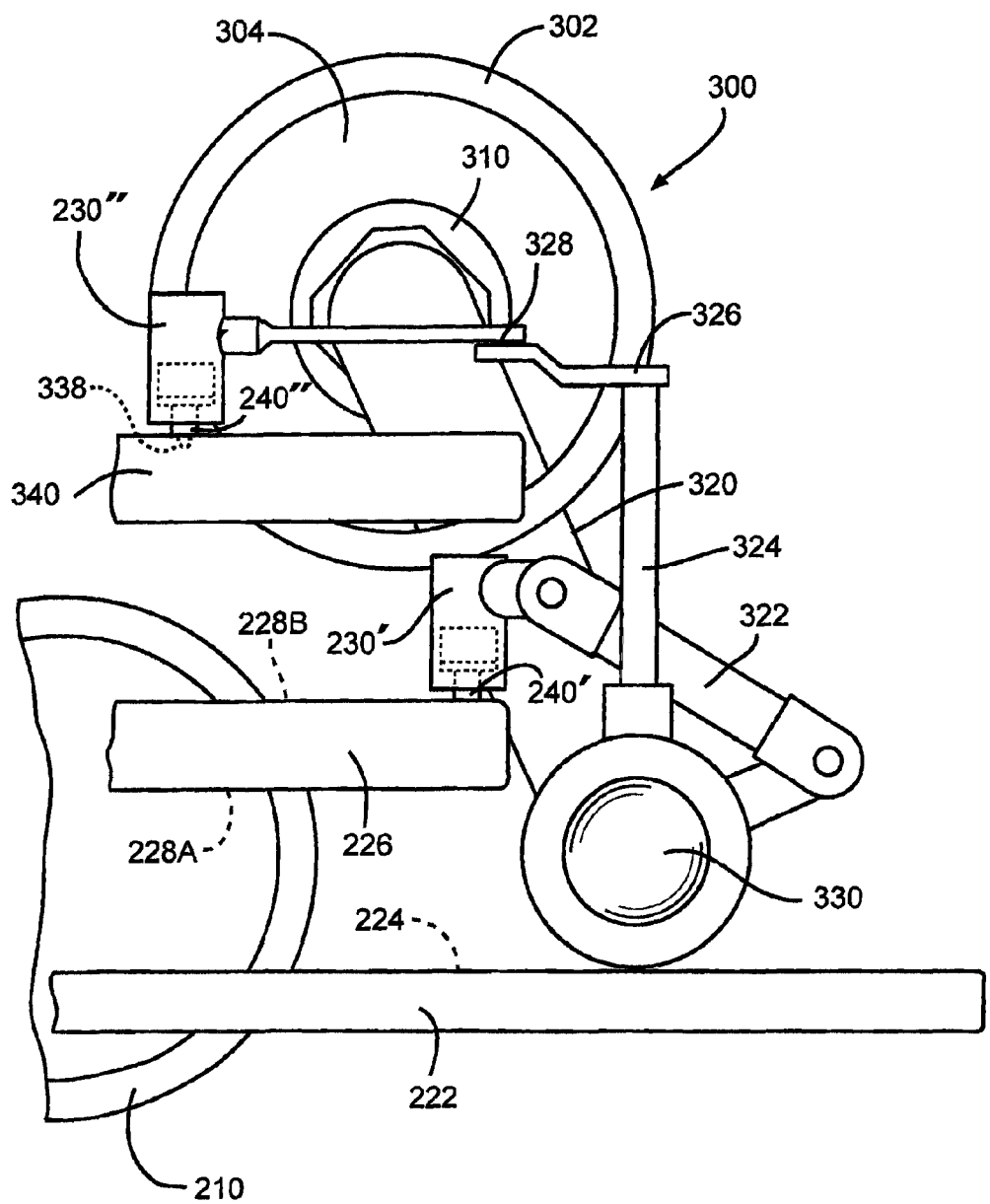
Figure 14:
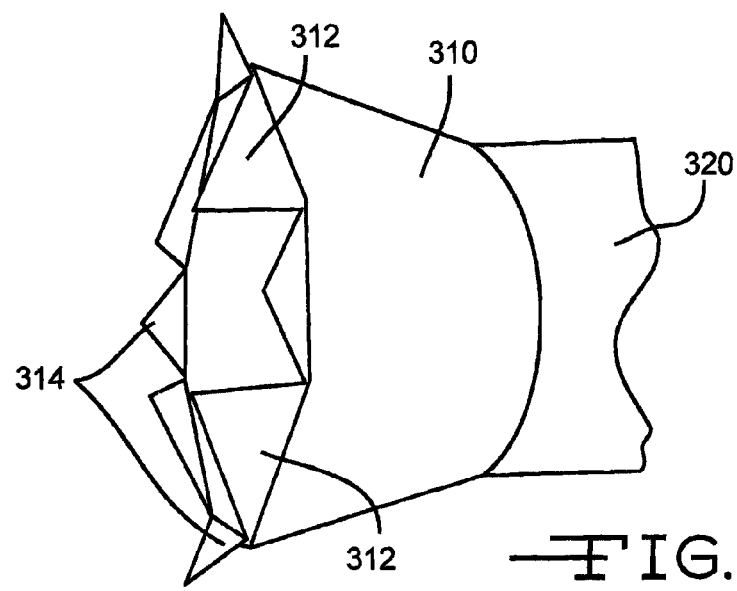
Figure 15:
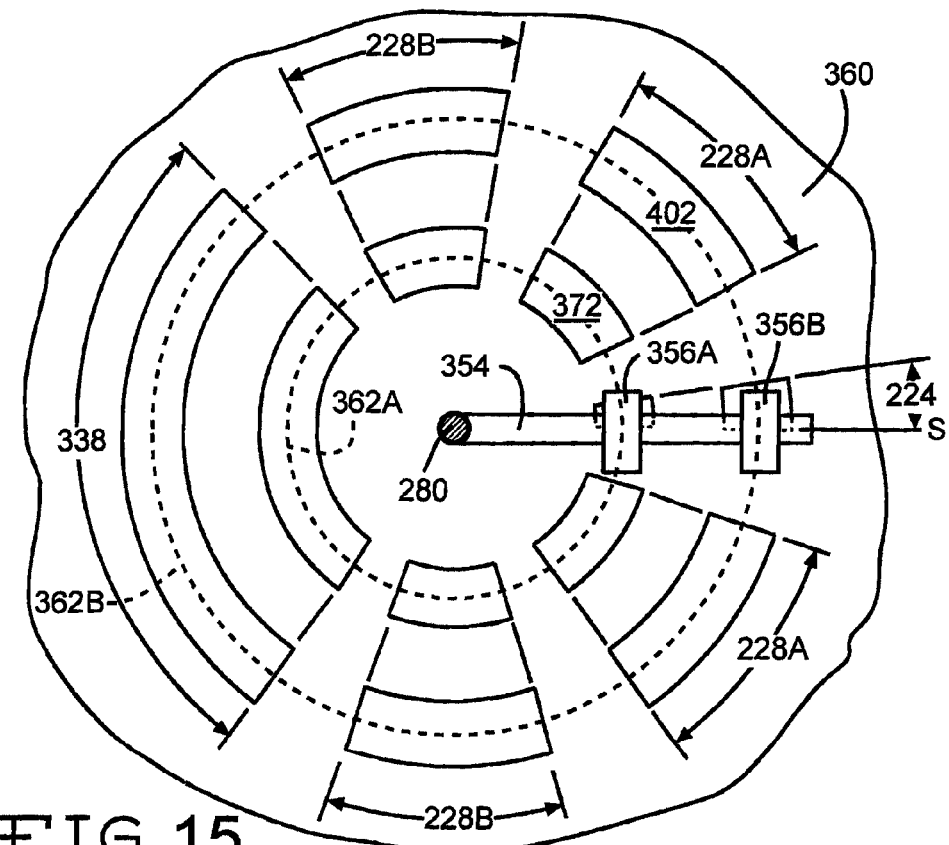
Figure 16A:
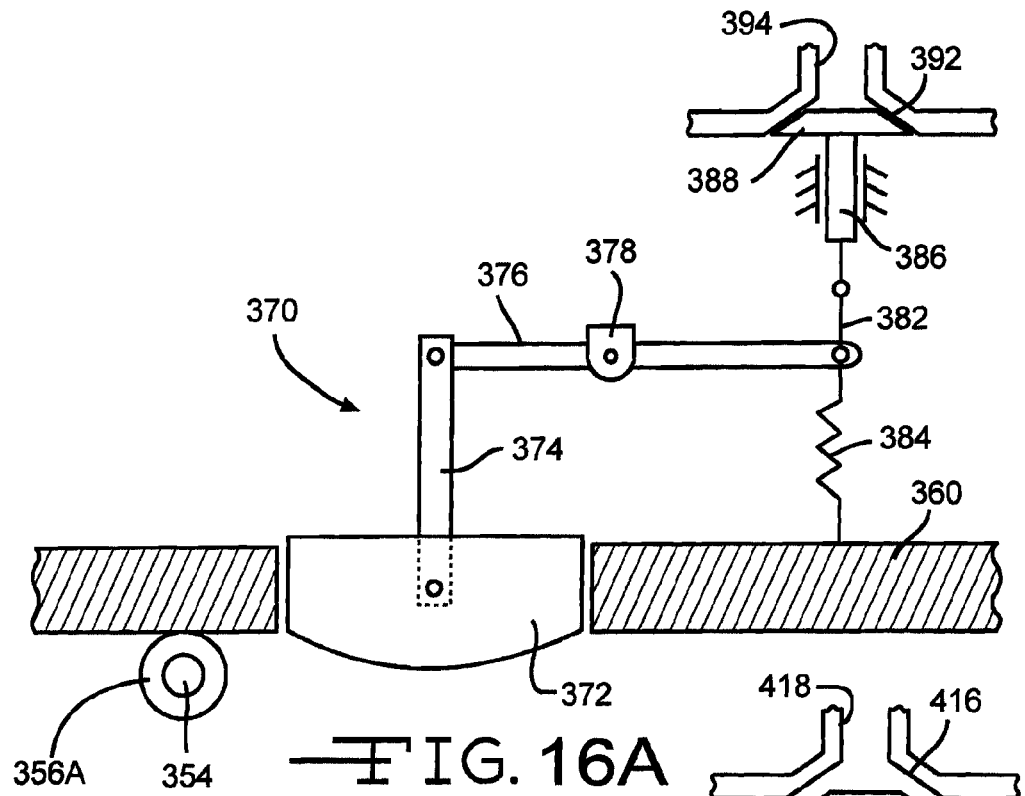
Figure 16B:
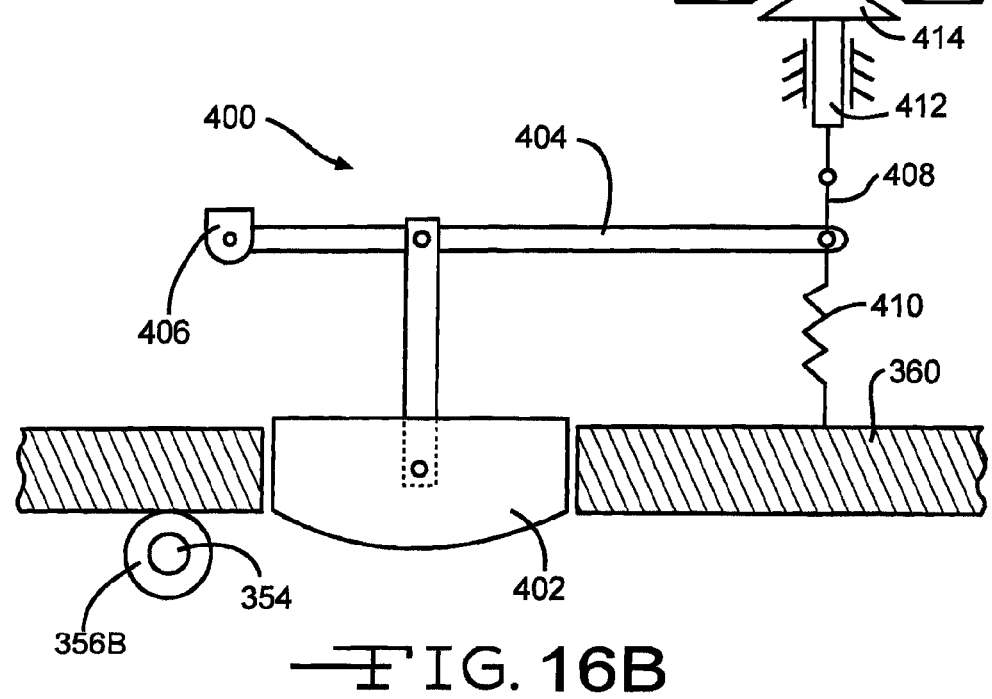

FIG. 3B enlarged view of an alternate embodiment of a piston head of a mass loading monitor according to the present invention;

FIG. 4 is a diagrammatic presentation of a deformable control volume relating to a mass loading monitor according to the present invention;

FIG. 5 is a graph of the outputs versus time of an accelerometer installed in the main piston of a mass loading monitor and a hot-wire anemometer installed at the end of the surrounding cylinder of a mass loading monitor according to the present invention demonstrating the theory of operation;

FIG. 6 is an electronic circuit block diagram illustrating the components and functions of a microprocessor or minicomputer for a mass loading monitor according to the present invention;

FIG. 7 is a schematic view of a second embodiment of a mass loading monitor according to the present invention;

FIG. 8 is a top plan view of a portion of the mass loading monitor illustrated in FIG. 7 including the cylinder, the piston and a cam for accelerating the piston;

FIG. 9 is a bottom plan view of a portion of the mass loading monitor illustrated in FIG. 7 including the cylinder, the piston and a cam for translating the piston to receive a charge of particulate laden air in the cylinder;

FIG. 10 is a full sectional view of a cam follower arm according to the present invention having active cam follower pins;

FIG. 11 is a top plan view of a portion of a jet ejector assembly, cam and cam follower according to the present invention;

FIG. 12 is an perspective view of ejector nozzle motion at the end of the cylinder according to the present invention;

FIG. 13 is an end elevational view of the jet ejector assembly according to the present invention showing the control valve, cams and linkages;

FIG. 14 is an enlarged perspective view of a tabbed nozzle of the jet ejector assembly according to the present invention;

FIG. 15 is a bottom plan view of a circular cam plate and cams according to the present invention disposed within a plenum which provides sequencing of the active cam follower pins;

FIG. 16A is a schematic view of a normally closed cam to valve linkage disposed within the plenum which provides activation of certain cam follower pins; and FIG. 16B is a schematic view of a normally open cam to valve linkage disposed within the plenum which provides activation of certain cam follower pins.

DETAILED DESCRIPTION

The following description is merely exemplary in nature and is not intended to limit the present disclosure, application, or uses.

Figure 1:
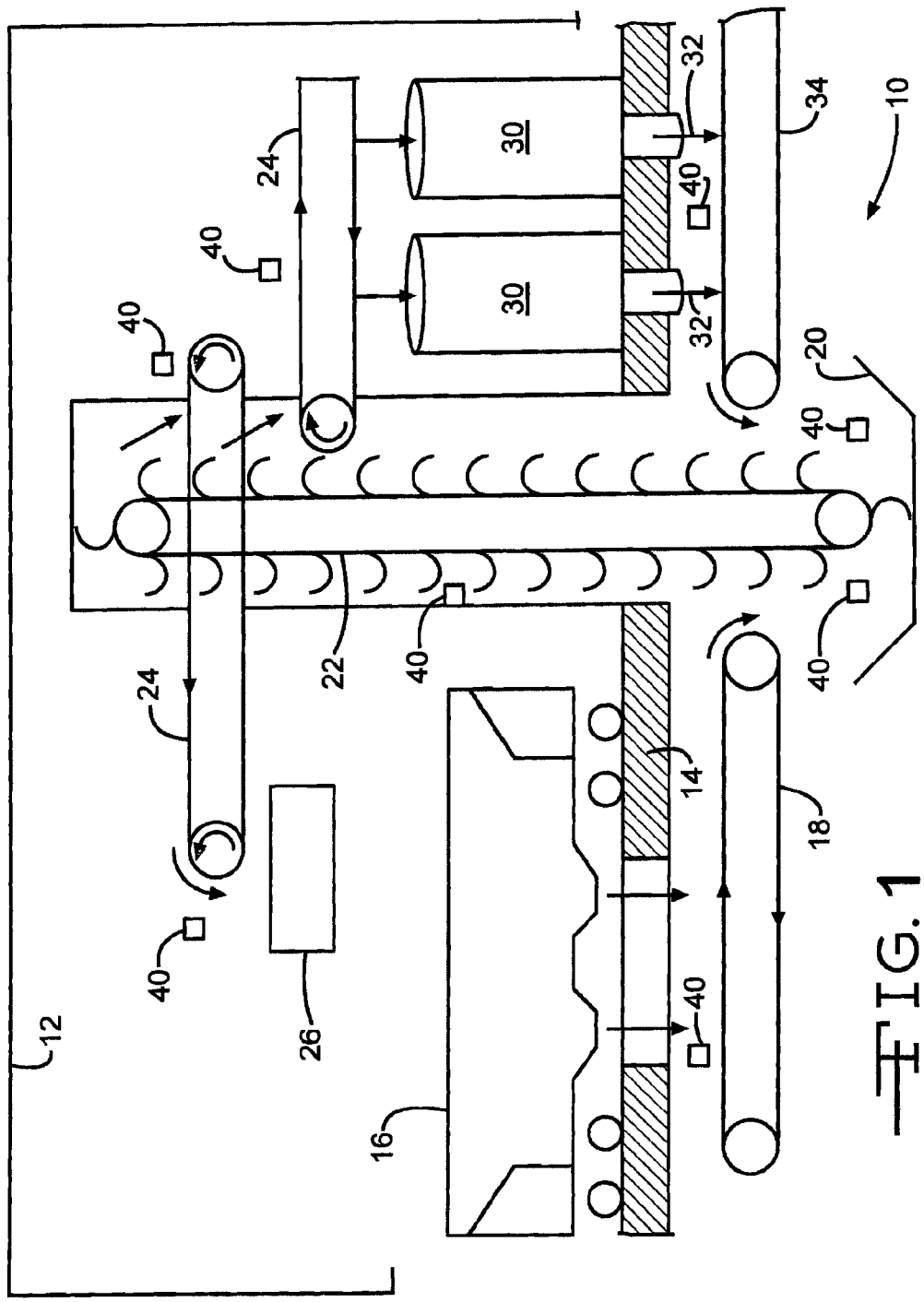
FIG. 1 is a schematic view of a grain processing facility indicating desirable locations for a mass loading monitor according to the present invention.

With reference to FIG. 1, a typical and exemplary grain processing facility is illustrated and designated by the reference number 10. At the outset, it should be understood that, for purposes of the present invention and description, the grain processing facility 10 is representative of any industrial or commercial facility such as a sawmill, furniture factory, sugar processing plant, cereal plant, or coal handing facility wherein dust, powder or other relatively fine particulate matter is generated and dispersed into the air.

The grain processing facility 10 includes a building or superstructure 12 which typically encloses the processing machinery which is installed on one or more floors 14. Railway gondola cars 16, trucks or other vehicles may supply raw material(s) to the facility 10 and dump their contents onto one or more horizontal conveyors 18. The conveyors 18 carry the material to a bin or hopper 20 from where they are extracted by a vertical, bucket type conveyor 22 or similar device. Cooperating horizontal conveyors 24 then carry the material to, for example, grinding or milling equipment 26 for processing or to one or more silos 30 for storage. The silos 30 include controllable outlets 32 which selectively supply material to an additional conveyor or conveyors 34 which, for example, provide material to the bin or hopper 20 or other collecting points.

At eight locations within the grain processing facility 10 are preferably disposed a mass loading monitor 40 according to the present invention. It will be appreciated, however, that more or fewer mass loading monitors 40 may be suitable or desirable in this exemplary facility 10, and that the actual number of monitors 40 preferred or necessary in a given facility will depend upon the construction and layout of the facility, upon its machinery, upon the nature of the material processed in the facility and other variables.

Figure 2A:
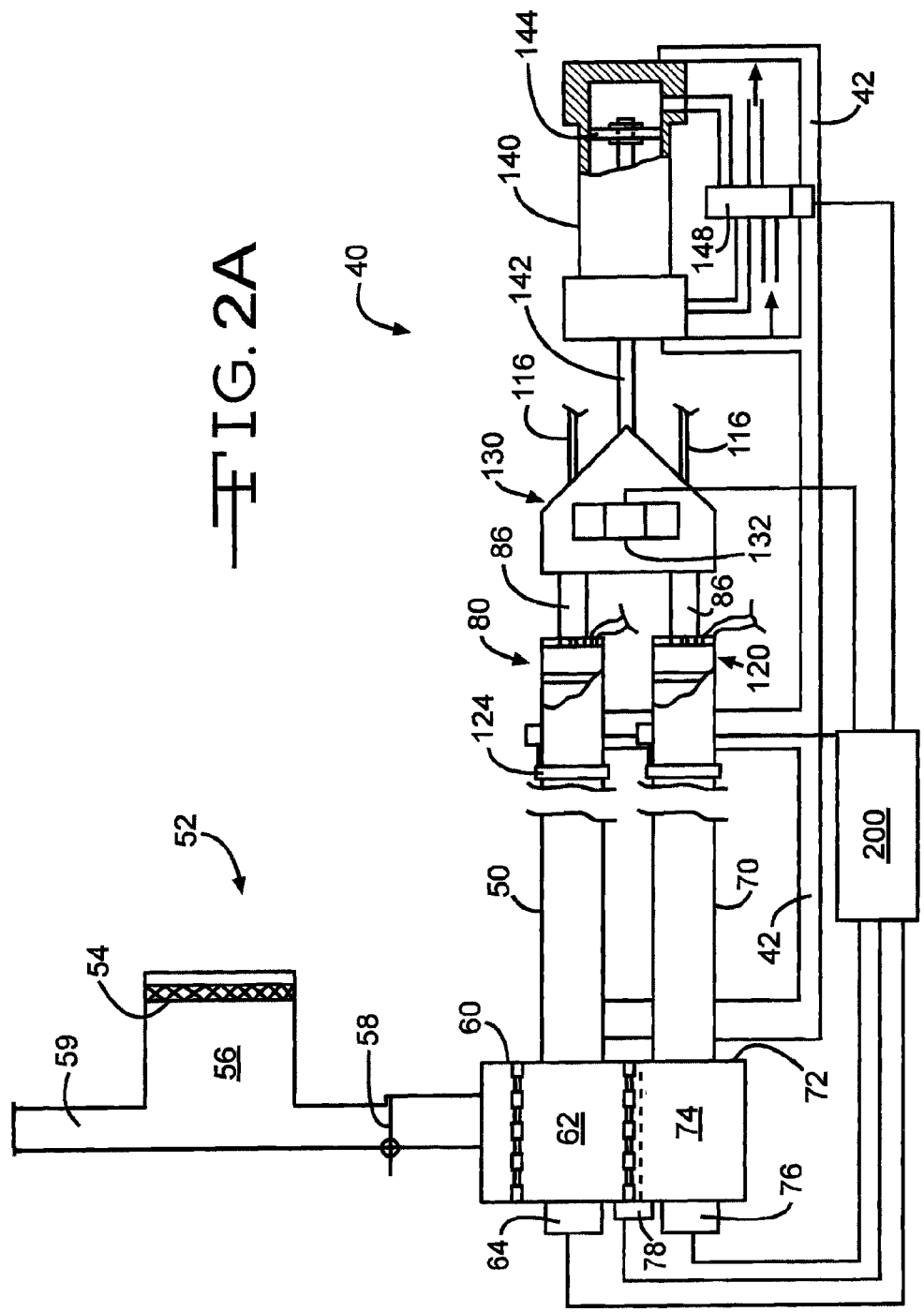
FIG. 2A is a schematic view of a first embodiment of a mass loading monitor according to the present invention.

Referring now to FIG. 2A, the mass loading monitor 40 includes an elongate frame 42 which supports a pair of rigid, parallel, elongate cylinders 50 having a length of approximately one meter. The first cylinder 50 is a clean air or reference cylinder and is supplied with clean ambient temperature and humidity air from an air supply 52 that includes a filter 54, a reservoir 56 and a check valve 58 to prevent backflow through the reservoir 56 and the filter 54. The air supply 52 and specifically the reservoir 56 may also include one or more additional outlet ducts or conduits 59 to provide clean air to one or more additional mass loading monitors 40, as, for example illustrated in FIG. 1. It should thus be appreciated that a single properly sized air supply 52 may service multiple mass loading monitors 40 or that individual air supplies 52 may by associated with and supply individual mass loading monitors 40, An open end of the first cylinder 50 is enclosed within a first valve or control box 60. The air supply 52 communicates with the interior of the first control box 60 as does the open end of the first cylinder 50. A first hinged panel 62 controlled by a first two position actuator 64 opens and closes the first hinged panel 62 which acts as a valve to allow the air within the first cylinder 50 to be exhausted to the ambient through the control box 60.

The second cylinder 70 which is essentially identical to the first cylinder 50 is a measurement cylinder and is supplied with air that contains dust, powder or other particulate matter from a region of a facility such as the grain processing facility 10. The open end of the second cylinder 70 is enclosed within a second valve or control box 72. A second hinged panel 74 is controlled by a second two position actuator 76. The second hinged panel 74 opens and closes to allow the particulate laden ambient air to be drawn into the second cylinder 70 through the control box 72 and to be exhausted (returned) to the ambient. A third hinged panel and two position actuator 78 provide selective communication between the first valve or control box 62 and the second valve or control box 74 to allow clean air into the second control box 74 and the second cylinder 70.

Figure 2B:
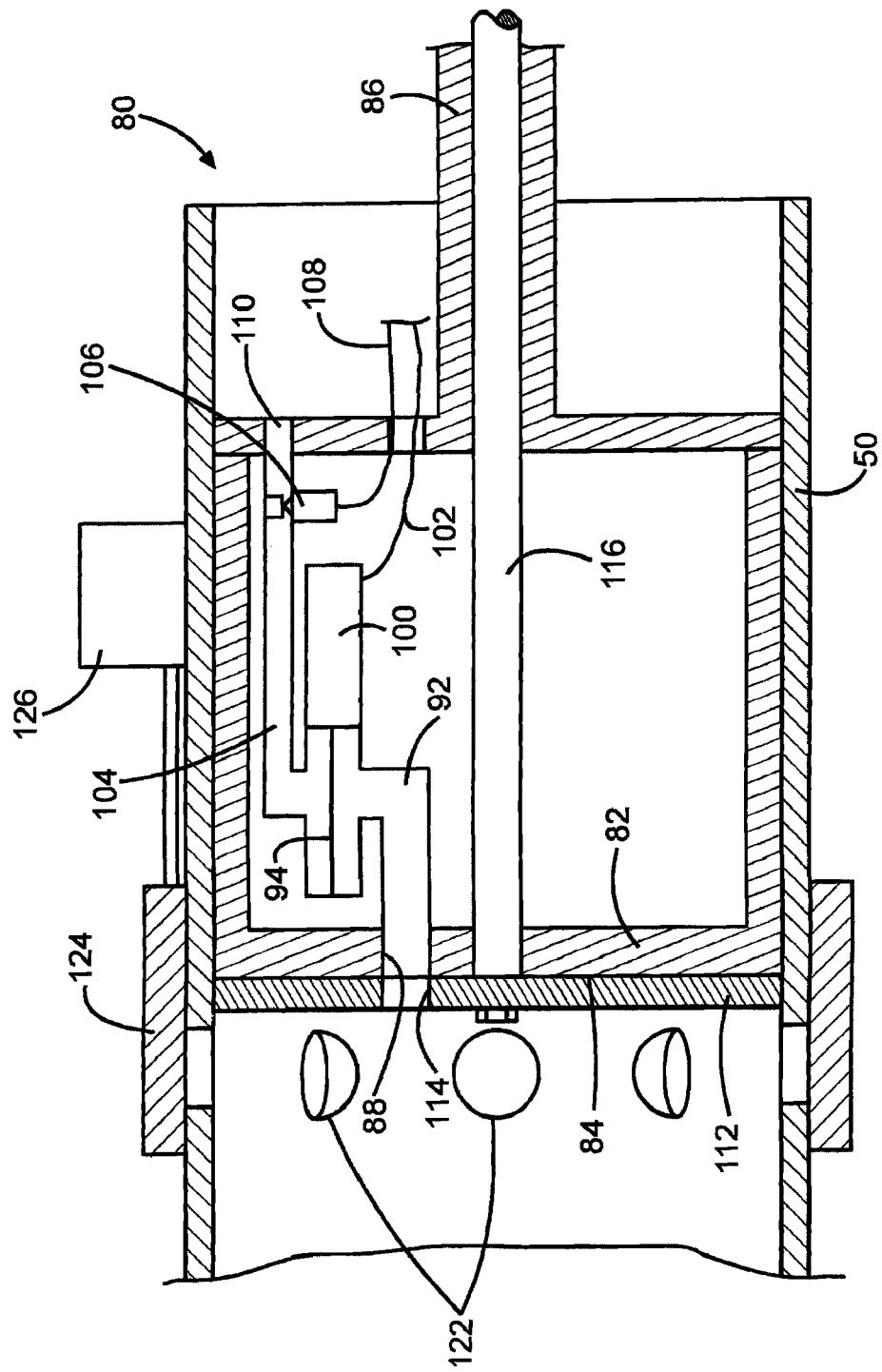
FIG. 2B is an enlarged view of a dual piston head of a mass loading monitor according to the present invention.

Referring now to FIGS. 2A and 2B, within the cylinders 50 and 70 are disposed respective piston assemblies: a first piston assembly 80 within the first cylinder 50 and a second piston assembly 120 within the second cylinder 70. Except for their dispositions in the first cylinder 50 and the second cylinder 70, the first and second piston assemblies 80 and 120 are identical and thus only the first piston assembly 80 will be described, it being understood that the description applies with equal accuracy to the second piston assembly 120.

As illustrated in FIG. 2B, the first piston assembly 80 includes a main or primary piston 82 which is preferably hollow to reduce weight and includes a flat face 84 at its front and a concentric drive tube or hollow shaft 86 at its rear. On the flat face 84 of the main piston 82 is a circular aperture or port 88 which communicates with an inlet passageway 92. In fluid communication with the inlet passageway 92 and oriented parallel to the axis (of translation) of the main piston 82 is a diaphragm 94 of a MEMS pressure transducer 100. The MEMS pressure transducer 100 preferably has a range of from 0.0 kPa to about 1.0 kPa and includes a multiple conductor output cable 102 which carries electrical energy and output signals or data from the transducer 100. On the side of the diaphragm 94 opposite the inlet passageway 92 is a reservoir passageway 104 which communicates with a two position (on-off) valve 106. A multiple conductor cable 108 provides electrical energy to the two position valve 106 to selectively operate it. On the opposite side of the two position valve 106 from the reservoir passageway 104 is an ambient pressure passageway and port 110. When the two position valve 106 is energized and open, ambient (atmospheric) pressure is established within the reservoir passageway 104. When the two position valve 106 is de-energized and closed, ambient (atmospheric) pressure is stored in the reservoir passageway 104.

Disposed adjacent the flat face 84 of the main piston 82 in a rest or quiescent position but moveable axially relative thereto is a light or secondary piston 112. The light piston 112 includes a circular aperture or port 114 which is preferably the same size as the circular aperture or port 88 on the main piston 82 and is aligned therewith as illustrated in FIG. 2B. Secured to the center of rear face of the light piston 112, extending axially therefrom and through the main piston drive tube or hollow shaft 86 is a light piston drive rod or shaft 116.

An annular band of a plurality of ports or apertures 122 extend around each of the cylinders 50 and 70 at an axial location just beyond the limit of translation of the main pistons 82. The ports or apertures 122 may be round, as illustrated, rectangular or another configuration. Extending about the circumference of each of the cylinders 50 and 70 in general alignment with the ports or apertures 122 is an axially, bi-directionally movable sleeve 124. In the position illustrated in FIG. 2B, the sleeve 124 closes off the ports or apertures 122. A two position actuator 126 translates the sleeve 124 to the right in FIG. 2B and opens the ports or apertures 122, allowing ambient air to enter or exit the cylinders 50 and 70.

Referring again to FIG. 2A, the main piston drive tube or hollow shaft 86 and the light piston drive rod or shaft 116 of the first piston assembly 80 and the main piston drive tube or hollow shaft 86 and the light piston drive rod or shaft 116 of the second piston assembly 120 extend to a light piston drive assembly 130. The main piston drive tube or hollow shaft 86 of the first piston assembly 80 and the main piston drive tube or hollow shaft 86 of the second piston assembly 120 are secured directly to and translate with the light piston drive assembly 130. The light piston drive rod or shaft 116 from the first piston assembly 80 and the light piston drive rod or shaft 116 from the second piston assembly 120, however, are connected to and translated in unison by one or a pair of bi-directional linear actuators or motors 132. The linear actuators or motors 132 may be electrically, hydraulically or pneumatically powered and capable of translating the light pistons 112 and the light piston drive shafts 116 approximately 3 feet (1 meter). The light piston drive assembly 130 and the main pistons 82 are, in turn, translated by a linear drive motor 140. The linear drive motor 140 may be any currently available linear energy source capable of accelerating the first and second pistons assemblies 80 and 120 at approximately 100 to 150 meters/sec/sec over a relatively short (approximately 1 inch (2 to 3 cm.)) distance such as a tension spring actuator, electric linear motor or hydraulic cylinder but is preferably a double acting pneumatic piston and cylinder assembly. As such, the linear drive motor 140 includes a single output rod or shaft 142 having a piston 144 secured thereto which is coupled to and bi-directionally drives the light piston drive assembly 130 and the main piston.

When the linear drive motor 140 is activated, the first and second main pistons 82 and the first and second light pistons 112 translate together in the respective first and second cylinders 50 and 70. To translate only the light piston drive rod or shaft 116 and the light piston 112 of the first piston assembly 80 and the light piston drive rod or shaft 116 and the light piston 112 of the second piston assembly 120, only the light piston drive assembly 130 is activated. The linear drive motor 140 also includes a control assembly 148 which directs pneumatic or hydraulic flow or the supply of electrical energy to the linear drive motor 140 to achieve such bi-directional translation as those skilled in the art will readily understand.

In an alternative construction illustrated in FIGS. 3A and 3B, the secondary pistons 112, the drive shafts 116, the light piston drive assembly 130, the ports 122, the sleeves 124 and the actuators 126 are eliminated. Accordingly, the first and second piston assemblies 80' and 120' which each include a main piston 82 which resides in the respective first and second cylinders 50 and 70, the main piston drive tubes 86' (which can be solid shafts rather than hollow tubes) and the linear drive motor 140 are utilized. In this construction, the main pistons 82 which are coupled to the output shaft 142 of the linear drive motor 140 by a bar or member 143 traverse essentially the full length of the respective cylinders 50 and 70 to ingest and expel clean air and particulate laden air. Given this extent of piston travel, hard wiring the MEMS pressure sensor 100 and the valve 106 to a stationary external data storage device or computer is impractical and thus a memory device and battery power supply 109 may be located within each of the main pistons 82 to record and subsequently download data. Alternatively, a low power, i.e., Bluetooth, transmitter may be incorporated in each of the main pistons 82 to provide real time data acquisition. Electrical contacts 111A on the pistons 82 which mate with aligned contacts 111B when the pistons 82 are fully retracted can also provide a data transfer route as well as provide electrical energy to the valve 106.

The mass loading monitor 40 is intended and designed to determine whether a particular concentration of particulate matter in the air of a facility such as the grain processing facility 10 is approaching the minimum explosive concentration (MEC). The MEC is specified as a density: X grams per cubic meter. The magnitude of X depends upon the material, for example, sugar, coal, sawdust, oats and wheat, and varies also with the relative humidity level. Nominal values are in the range of 30 to 80 grams per cubic meter. Typical sea level ambient density is on the order of 1.2 Kg per cubic meter and thus the resolution required is between 2.5 and 6.67%.

The measurement strategy of the mass loading monitor 40 follows from the recognition that a density difference ($\rho_w - \rho_{w/o}$) is sought and that discharging air with particulates (w) and without particulates (w/o) from a cylinder—by the action of an accelerating piston can yield ($\rho_w - \rho_{w/o}$). The following analysis illustrates how the pair of cylinders 50 and 70 can determine ($\rho_w - \rho_{w/o}$). Alternatively, a second embodiment 200, illustrated in FIGS. 7 through 16B, having a single cylinder can be utilized for this measurement.

Referring now to FIG. 4, the theory of operation and particulate mass measurement will be described in connection with a deformable control volume 150 disposed within the cylinder 70 that bounds or envelopes the particulate material. The momentum equation for this deformable control volume 150, unsteady flow condition, is $$\sum \vec{F} = \frac{d}{dt} \int_{cv} \rho \vec{V} \, dV + \int_{cs} \rho \vec{V} \vec{V} \cdot \hat{n} dA \qquad (1)$$

which leads to $$(p_p) A_p - \int_{x_p}^{L} \tau_w \pi D \, dx = \frac{d}{dt} \int_{cv} \rho u \, dV + \int_{exit} \rho u^2 \, dA \qquad (2)$$

where $p_p$ is the pressure at the face of the piston, $\tau_w$ is the wall shear stress, u and $\rho$ are the axial velocity and density of material within the cylinder 70. Experimental data reveal that the initial motion of the piston assemblies 80 and 120 compress and displace the air in the cylinders 50 and 70 in a progressive manner. That is, there is a time lag (approximately 0.01 sec. as presented in FIG. 5) for the air to be expelled from the 0.965 meter long cylinders 50 and 70. This time lag allows the spatially averaged density in the cylinders 50 and 70 to be assessed. Specifically, from Equation (2), the efflux term is zero for t<δt and Equation (2) can be integrated to provide (where T≦δt)

$$\underbrace{\int_{x_p}^{L} \rho u \, dx \Big|_{T}}_{(\alpha)} - \underbrace{\int_{x_p}^{L} \rho u \, dx \Big|_{0}}_{=0} = \underbrace{\int_{0}^{T} \int_{A_p} p \, dA \, dt}_{(\beta)} - \underbrace{\pi D \int_{0}^{T} \int_{x_p}^{L} \tau_w \, dx \, dt}_{(\gamma)} \qquad (3)$$

The "small" dust or powder loading ($\leq 80$ g/m$^3$) with respect to the density of the ambient air ($\approx 1.1$ Kg/m$^3$) makes it rational to assume that the term $\gamma$ will be unaffected by the presence or absence of particulate matter in the cylinders 50 and 70. In contrast, the basis for the measurement process is the dependence of the terms $\alpha$ and $\beta$ on the presence or absence of particulate matter. The two conditions are designated by the symbols: with particulates ( )$_w$: $\alpha$, $\beta$ and without particulates ( )$_{w/o}$: $\alpha$, $\beta$.

During calibration or at any time during its service life, the mass loading monitor 40 can be operated with clean air in both cylinders 50 and 70 to quantify minor differences in their operating characteristics. Specifically, the operating theory and computations presented herein do not require identical performances for ($\alpha$), ($\beta$) and ($\gamma$) with identical cylinder charges of no particulates although this will be assumed for the analytical structure of the data processing. The correction scheme, to be utilized when the air only data are not the same for the cylinders 50 and 70, is to first form the ratio: $[\beta_1/\beta_2]^*$, where $\beta_2$ represents the cylinder 70 that ingests the particulate matter. Second, when the dust or powder loading is to be determined, the ratio of the measured $\beta_2$ and $\beta_1$ values will then be multiplied by $[\beta_1/\beta_2]^*$ as a correction coefficient. It is understood that $\beta$ will represent the corrected $\beta_2$ value in the subsequent text.

The air in both cylinders 50 and 70 will be at the same temperature and pressure (hence the same density). From Equation 3, the ratio of the ($\alpha$) terms can be equated to the ratio of the spatially averaged densities since the integrals have identical kinematic features. This is the key step in the mass loading monitor 40 data processing algorithm. It should be appreciated that the time lag to accelerate the airborne particulate matter within the cylinder 70 will not only be small, but evaluating $\alpha$ at the discrete time T also ensures that the acceleration period will not alter the $\alpha$ value.

The desired information: $\Delta \rho = \langle \rho_w \rangle - \langle \rho_{w/o} \rangle$, can be obtained from the ratio $\alpha'/\alpha = \langle \rho_w \rangle / \langle \rho_{w/o} \rangle$ and the separately measured $\rho$. That is, a barometric pressure reading ($p_{atm}$) and the ambient (absolute) temperature T can provide ($\rho_{w/o}$) as: $\rho_{w/o} = p_{atm}/RT$, and $$\Delta \rho = \rho_{w/o} \frac{\langle \rho_w \rangle}{\langle \rho_{w/o} \rangle} - \rho_{w/o}. \qquad (5)$$

From measured data (where $\beta_w$ represents the corrected $\beta_2^*$ value)

$$\frac{\langle \rho_w \rangle}{\langle \rho_{w/o} \rangle} = \frac{\alpha_w}{\alpha_{w/o}} = \frac{\beta_w - \gamma}{\beta_{w/o} - \gamma} = \frac{\beta_w}{\beta_{w/o}} \left[ 1 + \frac{\gamma}{\beta_{w/o}} + \frac{\gamma^2}{\beta_{w/o}^2} + \frac{\gamma^3}{\beta_{w/o}^3} + \ldots \right] \qquad (6)$$

The ratio $\gamma/\beta$ is plausibly <1 since $\gamma$ depends upon the viscosity of air and the large acceleration (about 15 g's) will create an inertially dominated flow field. With this condition, it is recognized that the bracketed term represents a converged series whereby the bracketed term can be expressed as $$\frac{\rho_w}{\rho_{w/o}} = K \frac{\beta_w}{\beta_{w/o}} \quad (7)$$

The coefficient K can be treated as a calibration constant. Known quantities of small particulates can be added to a vertically disposed cylinder 70 and the piston 120 accelerated before their "leading edge" reaches the piston face. Since $(\alpha_w/\alpha_{w/o})$ will therefore be known and $(\beta_w/\beta_{w/o})$ will be measured, K can be determined.

Referring now to FIG. 5, a graph illustrates the time difference between the acceleration of one of the main pistons 82 and the later air motion at the end of the associated cylinder 50 or 70. The left vertical scale is the voltage output of an accelerometer and relates to the left plot 162. The horizontal scale is time in seconds. The right plot 164 is data from a hot-wire anemometer located at the end of the same cylinder 50 or 70, at the control box. The plot 164 indicates that motion of the air at the end of the cylinders 50 and 70 commences after the acceleration of the main pistons 82 (and measurement of air within the cylinders 50 and 70) has been completed.

Referring now to FIGS. 2A, 2B and 6, an electronic circuit block diagram of a mass loading monitor 40 is illustrated and designated by the reference number 170. At the outset, it should be appreciated that sequencing of the operation of the mass loading monitor 40 described herein as well as data acquisition and storage is preferably under the control of a personal computer or microprocessor 200. In operation, the light piston drive assembly 130 is activated to translate the light pistons 112 to the left, the length of the cylinders 50 and 70, and then to the right to charge the first cylinder 50 with clean air. The sleeve actuator 126 is also energized to translate the sleeve 124 and open the ports 122 to allow air behind the faces of the light pistons 112. The actuator 76 is energized during the return stroke of the light piston drive assembly 130 to provide particulate laden ambient air into the second cylinder 70. The linear drive motor 140 is then activated to rapidly accelerate the light pistons 112 and the main pistons 82 a short distance, i.e., two to three centimeters, along the cylinders 50 and 70. During this time, the MEMS transducers 100 in the main pistons 82 in the first, clean air cylinder 50 and the second, measurement cylinder 70 sense the pressure at the face of the light pistons 112 and provide these data to an analog to digital converter 172. The digital data are then provided to integrators 174 which integrate the pressure from the beginning of the accelerative run of the piston assemblies 80 and 120 (t=0) to the end (t=T).

The ratio of the integrands from the integrators 174 is then established in a comparator 176 and this value is multiplied by the constant K in a process (multiplier) step 178. A programmable or read only memory or storage device 182 includes look up tables and other data utilized, for among other purposes, to calculate the minimum explosive concentration (MEC). The MEC, as noted above, varies with the type of material, for example, sugar, coal, sawdust, oats and wheat, and varies also with the relative humidity. This current, necessary information is provided to a computational comparator 184 in which the value of the stored MEC is multiplied by a safety factor δ to avoid a false negative indication and this value is subtracted from $K(\beta_w/\beta_{w/o})$. If the result is greater than or equal to one, a warning signal is provided by an annunciator 186. If the result is less than one, no output or a null or safe signal may be provided by an annunciator 188. Alternatively, as noted above, the warning signal may directly control operations within a processing facility and shut down the machinery generating the MEC without human intervention.

The mechanical cycle of the piston assemblies 80 and 120 of the embodiment illustrated in FIGS. 2A and 2B is completed by retraction of the main pistons 82 through reverse operation of the linear drive motor 140, opening the sleeves 124, translation of the light pistons 112 to the ends of the cylinders 50 and 70, reverse translation of the light pistons to draw in new air charges into the cylinders 50 and 70 and closing of the sleeves 124, whereupon the mass loading monitor 40 is prepared for a new measurement. With regard to the embodiment illustrated in FIGS. 3A and 3B, the main pistons 82 may complete a traverse of the cylinders 50 and 70 to the left to expel the present charges and then translate to the right to ingest a fresh charge of clean air and particulate laden air, respectively.

Operation of the alternate construction illustrated in FIGS. 3A and 3B is essentially the same. The control assembly 148 is activated to provide compressed air to the linear drive motor 140 to translate the piston 144 fully to the left in FIG. 3A and then to the right to charge the cylinders 50 and 70 with clean and particulate laden air, respectively. The linear drive motor 140 is then activated to rapidly accelerate the main pistons 82 a short distance, i.e., two to three centimeters, along the cylinders 50 and 70. During this time, the MEMS transducers 100 in the main pistons 82 in the first, clean air cylinder 50 and the second, measurement cylinder 70 sense the pressure at the face 84 of the main pistons 82 and provide these data to the memory device and battery power supply 109.

Referring now to FIG. 7, a second embodiment of a mass loading monitor according to the present invention is illustrated and generally designated by the reference number 200. The second embodiment of the mass loading monitor 200 includes a frame 202 which extends along and supports the components and assemblies of the mass loading monitor 200 including, an elongate cylinder 210 having a length and diameter like the cylinders 50 and 70 of the first embodiment mass loading monitor 40, a cam and drive assembly 220, a jet ejector assembly 300 and a sequencing assembly 350 housed in a plenum 352. If desired, the mass loading monitor 200 may be enclosed in an outer housing 204 having suitable access and service panels (not illustrated).

Referring now to FIGS. 3B, 7, 8, 9 and 10, the cylinder 210 includes a plurality of generally rectangular ports or access openings 212 which encircle the cylinder 210 proximate an end adjacent the cam and drive assembly 220. At the opposite end of the cylinder 210 is the jet ejector assembly 300. Closely fitting with the smooth walled interior of the cylinder 210 is a wireless piston assembly 80' including a piston 82 and the other components contained therein and illustrated in FIG. 3B. Alternatively, a hard wired piston assembly utilizing the piston assembly 80' but with hard wiring extending to remote equipment may be utilized in view of the relatively limited travel of the piston assembly 80' in the second embodiment mass loading monitor 200. The piston 82 is secured to a connecting rod 214 which extends into a space between a first drive disc 222 and a second drive disc 226 of the cam and drive assembly 220 and terminates in a double cam follower assembly 230.

The double cam follower assembly 230, illustrated in FIG. 10, is an active, air powered device having a cylindrical housing 232 oriented perpendicularly to the axis of the connecting rod 214 which defines a first or lower cylinder 234, accessed by a pair of spaced-apart ports 236A and 236B, which receives a first double acting piston 238 connected to a first, lower cam follower 240 which terminates in a friction reducing ball bearing assembly 242. Similarly, the housing 232 defines a second or upper cylinder 244, accessed by ports 246A and 246B, which receives a second double acting piston 248 connected to a second, upper cam follower 250 which terminates in a friction reducing ball bearing assembly 252. A plurality of lugs or bosses 254 or similar structures at the ends of the cylinders 234 and 244 prevent the respective pistons 238 and 248 from bottoming out, closing off the ports 236A, 236B, 246A and 246B and inhibiting translation of the pistons 238 and 248 when compressed air is supplied to the ports 236A, 236B, 246A and 2466.

The first drive disc 222 includes a first complex cam track 224 utilized to rapidly accelerate the piston assembly 80' to undertake a measurement as will be more fully described subsequently. The second drive disc 226 includes a second, bell shaped cam track 228A utilized to translate the piston assembly 80' in cooperation the jet ejector assembly 300 to draw particulate laden air into the cylinder 210. When commanded, either the first, lower cam follower 240 is extended downwardly to engage the first complex cam track 224 to undertake a measurement of β or the second, upper cam follower 250 is extended upwardly to engage the second cam track 228A to facilitate ingestion of particulate laden air into the cylinder 210 as will be more full described subsequently.

Referring now to FIGS. 7, 11, 12, 13 and 14, the jet ejector assembly 300 includes an ejector nozzle 302 having an inlet end 304 defining an inside diameter equal to the inside diameter of the cylinder 210 such that, as illustrated in FIG. 7, the ejector nozzle 302 may be aligned and disposed at the end of the cylinder 210 with minimal flow disruption at their junction. The nozzle 302 has a venturi configuration and disposed proximate a throat 306 is a tabbed jet array 310 which generates streamwise vorticity and enhances mixing. The jet array 310 includes alternating larger, inwardly directed tabs 312 and smaller, outwardly directed tabs 314, all having side angles of 45°. The jet array 310 is connected to, supported by and supplied pressurized air through a pipe or conduit 320 which extends perpendicularly through the wall of the ejector nozzle 302 and extends along the cylinder 210 to the cam and drive assembly 220.

As illustrated in FIGS. 11 and 13, the pipe or conduit 320 is attached to a follower arm 322 which terminates in a first, single cam follower assembly 230'. The first, single cam follower assembly 230' is similar to the double cam follower assembly 230 illustrated in FIG. 10 except that it includes only the lower cylinder 234, the ports 236A and 236B, the double acting piston 238, a vertically moveable lower cam follower 240' and the ball bearing assembly 242. The lower cam follower 240' selectively engages a third cam track 228B on the upper side of the second drive disc 226. If the first, single cam follower assembly 230' is activated such that the lower cam follower 240' is disposed in the third cam track 228B, as the second drive disc 226 rotates, the ejector nozzle 302 moves into or out of position at the open end of the cylinder 210 as illustrated in FIG. 12 and described more fully below.

Referring now to FIGS. 7 and 13, the jet ejector assembly 300 also includes a ball valve 330 in the pipe or conduit 320 which selectively opens to deliver compressed air to the tabbed jet array 310 in the ejector nozzle 302. The ball valve 320 includes a shaft 324 which is secured to a crank 326 and a linkage arm 328 which terminates in a second, single cam follower assembly 230". The second, single cam follower assembly 230" is the same as the first, single cam follower assembly 230' and includes a vertically moveable cam follower 240". The cam follower 240" selectively engages a fourth cam track 338 on a third drive disc 340. If the second, single cam follower 230" is activated, rotation of the third drive disc 340 opens or closes the ball valve 330 as described more fully below.

Referring again to FIG. 7, the cam and drive assembly 220 includes an electric motor 260 having an output shaft 262 that directly drives a first timing belt drive pulley 264, a flywheel 266 and the first drive disc 222. Both the motor 260 and the output shaft may be supported by the frame 202. The first timing belt drive pulley 264 drives a larger, first driven timing belt pulley 268 through a first timing belt 270. The sizes of the pulleys 264 and 268 accomplish a 4 to 1 speed reduction. The first driven timing belt pulley 268 is secured to an idler shaft 272. Also secured to the idler shaft 272 is a second timing belt drive pulley 274 which drives a larger, second driven timing belt pulley 276 through a second timing belt 278. The sizes of the pulleys 274 and 276 accomplish a 5 to 1 speed reduction. The second timing belt driven pulley 276 is secured to a drive shaft 280 which is part of the sequencing assembly 350. The drive shaft 280 of the sequencing assembly 350 rotates at one-twentieth the speed of the electric motor 260.

Secured to the upper end of the idler shaft 272 is a third timing belt drive pulley 284 which engages and drives a third timing belt 286. The third timing belt 286 engages and drives a third driven timing belt pulley 288. The sizes of the pulleys 284 and 288 are the same such that there is no speed increase or decrease between them. The third driven timing belt pulley 288 is secured to an upper shaft 290 which is coaxial with the output shaft 262 of the motor 260 and may be piloted therein in a suitable bearing assembly 292. Secured to the upper shaft 290 for rotation therewith are the second drive disc 226 and the third drive disc 340.

Referring now to FIGS. 7, 15, 16A and 16B, the sequencing assembly 350 is disposed in the plenum 352 and driven by the drive shaft 280. Secured to the drive shaft 280 is an actuator arm 354 upon which reside a pair of spaced-apart rollers 356A and 356B disposed adjacent a cam plate 360. The inner roller 356A aligns with an inner cam track 362A and the outer roller 356B aligns with an outer cam track 362B. The inner and outer cam tracks 362A and 362B include a plurality of circularly arranged arcuate cams that are actuated (depressed) by the rollers 356A and 356B as the drive shaft 280 and the actuator arm 354 rotate.

Normally closed valves are associated with the inner cam track 362A and normally open valves are associated with the outer cam track 362B. In FIG. 16A, a normally closed valve linkage 370 is illustrated and includes a cam 372 disposed in an opening in the cam plate 360. The cam 372 is coupled to a first link 374 which is coupled to a first class lever arm 376 having a pivot 378 and a second link 382 which is attached to a compression spring 384 at one end and a valve stem 386 at the other. A valve body 388 is attached to the valve stem 386 and seats within a valve seat 392. When the cam 372 is depressed, the valve body 388 moves off the seat 392 and provides a flow of compressed air to a passageway or line 394 which communicates with a port in a cam follower assembly.

In FIG. 16B, a normally open valve linkage 400 is illustrated and includes a cam 402 disposed in an opening in the cam plate 360. The cam 402 is coupled to a third class lever arm 404 having a pivot 406 and a link 408 that is connected at one end to a tension spring 410 and at the other end to a valve stem 412. A valve body 414 is attached to the valve stem 412 and seats within a valve seat 416. When the cam 402 is depressed, the valve body 414 moves against the seat 416 and terminates a flow of compressed air to a passageway or line 418 which communicates with a port in a cam follower assembly. The plenum 352 is preferably supplied with pressurized air, commonly referred to as "shop air" at pressures in the range of from 60 to 120 p.s.i. and more preferably in the range of 90 to 100 p.s.i.

The sequence of operation of the second embodiment mass loading monitor 200 will now be presented with reference to all of the drawing Figures, especially FIGS. 7 and 15. The cycle of operation starts with the piston 80' beyond, i.e., to the left of, the ports 212, in the position illustrated in FIGS. 7 and 8, with a charge of particulate laden air in the cylinder 210. From the start position at three o'clock in FIG. 15 indicated by an "S", the following events sequentially occur:

| Rotation of Disc 222 | Cam Track | Actuator Motion | Action |
|---|---|---|---|
| 0.5 | 224 | Down | Piston 80' accelerates to 10 g's, then retracts |
|  | 224 | Up | Piston 80' returns to start position |
| 1.0 |  |  | 360° dwell before next event |
| 2.0 | 228A | Up | Retract piston 80' behind ports 212 |
|  | 228A | Down | Hold piston 80' behind ports 212 |
| 1.0 |  |  | 360° dwell before next event |
| 2.0 | 228B | Down | Rotate pipe 320 to place ejector nozzle 302 on axis of cylinder 210 |
|  | 228B | Up | Retain nozzle 302 on axis |
| 1.0 |  |  | 360° dwell before next event |
| 5.5 | 338 | Down | Open ball valve 330 to bring new particulate laden air into cylinder 210 |
|  | 338 | Up | Close ball valve 330 |
| 1.0 |  |  | 360° dwell before next event |
| 2.0 | 228B | Down | Return nozzle 302 to off axis position |
|  | 228B | Up | Hold nozzle 302 in off axis position |
| 1.0 |  |  | 360° dwell before next event |
| 2.0 | 228A | Up | Move piston 80' to start position |
|  | 228A | Down | Hold piston 80' in start position |
| 1.0 |  |  | 360° dwell before starting next cycle |
| 20.0 |  |  | Rotations of first drive disc 222 |

At the completion of a measurement cycle as described directly above, data from the MEMS pressure sensor 100 within the piston 82 is downloaded or read, the time integral of pressure is computed and compared with the stored reference or calibration data and the particulate content of the air is computed.

As FIG. 15 graphically illustrates, the roller 356A sequentially activates cams such as the cam 372 in the inner cam track 362A which is associated with the normally closed valve linkages 370 and the valves 388. Likewise, the roller 356B sequentially activates cams such as the cam 402 in the outer cam track 362B which is associated with the normally open valve linkages 400 and the valves 414. The valves 388 and 414 provide or terminate the flow of compressed air to the upper cylinder 244 of the double cam follower assembly 230 associated with the second cam track 228A on the second drive disc 226 to advance and retract the upper cam follower 250. As illustrated in FIG. 15, additional normally closed and normally open valve linkages 370 and 400 are associated with the first cam track 224 on the first drive disc 222 to provide compressed air to the lower cylinder 234 and translate the lower cam follower 240, the third cam track 228B on the second drive disc 226 and its cam follower assembly 230' and the fourth cam track 338 on the third drive disc 340 and its cam follower assembly 230".

It should be understood that the sequencing assembly 350 may be replaced by an electronic timing or sequencing device (not illustrated) having, for example, an optical or magnetic marker attached to the first disc 222 and a proximate compatible sensor which provides timing or synchronizing pulses to a programmed sequencer such as a microprocessor having a plurality of outputs which drive solenoid valves on a manifold supplied with shop air and which selectively provide compressed air to the cam follower assemblies 230, 230' and 230" in accordance with the above described sequence of operation.

The description of the invention is merely exemplary in nature and variations that do not depart from the gist of the invention are intended to be within its scope. Such variations are not to be regarded as a departure from the spirit and scope of the invention

We claim:

1. An apparatus for measuring particulate concentration in air comprising, in combination,
    an elongate cylinder having a piston disposed therein, said piston having a face,
    means for supplying particulate laden air to said cylinder,
    means for translating said piston in said cylinder, and
    means for sensing pressure in said cylinder proximate said piston face during translation of said piston.

2. The apparatus of claim 1 further including a second piston disposed in a second cylinder disposed in parallel and having the same diameter as said elongate cylinder.

3. The apparatus of claim 2 wherein said means for translating is a pneumatic cylinder having a piston rod coupled to both of said pistons.

4. The apparatus of claim 2 wherein said means for translating is a single device having an output coupled to both of said pistons.

5. The apparatus of claim 1 wherein said means for translating is a rotating cam and a cam follower selectively engagable with said cam.

6. The apparatus of claim 1 further including means for storing sensed pressure data from said means for sensing pressures.

7. The apparatus of claim 1 further including means for transmitting sensed pressure data from said means for sensing pressures to a location remote from said cylinders.

8. The apparatus of claim 1 wherein said means for translating includes an electromagnetic device.

9. The apparatus of claim 1 further including a jet ejector assembly selectively postionable at an end of said cylinder.

10. An apparatus for measuring particulate concentration in air comprising, in combination,
    a measurement assembly having a cylinder and a piston defining a face disposed therein,
    an air supply for providing particulate laden air to said cylinder,
    drive means for translating said piston in said cylinder, said drive means accelerating said piston at a constantly increasing rate, and
    pressure sensing means associated with said piston for sensing pressure at said face of said piston during acceleration of said piston.

11. The apparatus of claim 10 further including means for storing and transmitting sensed pressure data from said means for sensing pressures.

12. The apparatus of claim 10 further including a plurality of ports in a wall of said cylinder, a sliding collar for selectively closing and opening said ports and an actuator for translating said collar.

13. The apparatus of claim 12 further including control means for sequencing operation of said means for translating said piston and said actuator.

14. The apparatus of claim 10 wherein said drive means includes an electromagnetic device.

15. The apparatus of claim 10 further including a jet ejector assembly selectively postionable at an end of said cylinder.

16. An apparatus for measuring particulate concentration in air comprising, in combination,
- an elongate cylinder defining a plurality of ports and having a piston disposed therein,
- a first drive assembly for translating said piston across said ports to allow particulate laden air to enter said cylinder,
- a second drive assembly for rapidly translating said piston in said cylinder, and
- means for sensing pressure in said cylinder proximate said piston during rapid translation.

17. The apparatus of claim 16 wherein said first and second drive assemblies include rotating cams and an active cam follower having selectively movable cam engaging pins.

18. The apparatus of claim 17 further including a motor for driving said first drive assembly, said second drive assembly and a sequencer for controlling said active cam followers.

19. The apparatus of claim 18 further including a speed reduction assembly operably disposed between said motor and said second drive assembly.

20. The apparatus of claim 16 further including a jet ejector assembly selectively postionable at an end of said cylinder.

* * * * *

UNITED STATES PATENT AND TRADEMARK OFFICE
CERTIFICATE OF CORRECTION

| | | |
|---|---|---|
| PATENT NO. | : 8,302,460 B2 | Page 1 of 1 |
| APPLICATION NO. | : 12/610827 | |
| DATED | : November 6, 2012 | |
| INVENTOR(S) | : John F. Foss and Alan R. Lawrenz | |

It is certified that error appears in the above-identified patent and that said Letters Patent is hereby corrected as shown below:

In the Specification

Col. 1, lines 18-19 should read

STATEMENT REGARDING FEDERALLY SPONSORED RESEARCH OR DEVELOPMENT

This invention was made with government support under Grant No. 2007-33610-18029 awarded by the United States Department of Agriculture. The United States government has certain rights in the invention.

Signed and Sealed this
Eleventh Day of November, 2014

Michelle K. Lee
*Deputy Director of the United States Patent and Trademark Office*